(12) United States Patent
Mariami

(10) Patent No.: US 8,783,525 B2
(45) Date of Patent: Jul. 22, 2014

(54) DRIVE MECHANISM FOR A DRUG DELIVERY DEVICE

(75) Inventor: Faiza Mariami, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 220 days.

(21) Appl. No.: 13/290,895

(22) Filed: Nov. 7, 2011

(65) Prior Publication Data

US 2012/0148425 A1 Jun. 14, 2012

(30) Foreign Application Priority Data

Nov. 19, 2010 (EP) .................................... 10191803

(51) Int. Cl.
| | | |
|---|---|---|
| *B67D 7/60* | (2010.01) | |
| *G01F 11/00* | (2006.01) | |
| *B67B 1/00* | (2006.01) | |
| *A61M 5/315* | (2006.01) | |

(52) U.S. Cl.
CPC ....... *A61M 5/31586* (2013.01); *A61M 5/31571* (2013.01)
USPC ........................ 222/390; 222/391; 222/153.13

(58) Field of Classification Search
CPC .......... A61M 5/31578; A61M 5/3158; A61M 5/31581; A61M 5/31583; A61M 5/31585; A61M 5/31586; A61M 5/31571; B05C 17/012; B05C 17/013; B05C 17/0133
USPC ............... 222/390, 392, 336, 153.13, 153.14, 222/153.09; 72/172–174; 604/209
See application file for complete search history.

(56) References Cited

U.S. PATENT DOCUMENTS

| | | | | |
|---|---|---|---|---|
| 2,086,462 A | * | 7/1937 | Bost | ................................. 433/90 |
| 4,368,830 A | * | 1/1983 | Soughers | ................. 222/153.13 |
| 4,641,766 A | * | 2/1987 | Vlasich | ......................... 222/391 |
| 4,658,993 A | * | 4/1987 | Vlasich | ......................... 222/390 |
| 4,710,178 A | * | 12/1987 | Henri et al. | .................... 604/209 |

(Continued)

FOREIGN PATENT DOCUMENTS

| | | |
|---|---|---|
| WO | 99/38554 | 8/1999 |
| WO | 2005/037352 | 4/2005 |
| WO | 2007/092929 | 8/2007 |
| WO | WO 2007092929 A2 * | 8/2007 |

OTHER PUBLICATIONS

European Search Report for EP App. No. 10191803, dated May 20, 2011.

*Primary Examiner* — Paul R Durand
*Assistant Examiner* — Benjamin R Shaw
(74) *Attorney, Agent, or Firm* — McDonnell Boehnen Hulbert & Berghoff LLP

(57) ABSTRACT

The present invention relates to a drive mechanism of a drug delivery device for dispensing of a dose of a medicament, comprising:
- a housing of substantially cylindrical geometry having a long axis extending in an axial direction,
- an at least axially displaceable piston rod adapted to become operably engaged with a piston of a cartridge containing the medicament for displacing the piston in a distal direction,
- at least one actuation means radially displaceable with respect to the housing by an externally applied depressing force for transferring a respective driving force to the piston rod, and
- a coupling means operably engaged with the actuation means and with the piston rod adapted to transfer the radially inwardly directed displacement of the at least one actuation means into a distally directed axial displacement of the piston rod.

11 Claims, 3 Drawing Sheets

(56) References Cited

U.S. PATENT DOCUMENTS

| | | | |
|---|---|---|---|
| 4,865,231 A * | 9/1989 | Wiercinski | 222/390 |
| 5,320,259 A * | 6/1994 | Weinstein | 222/391 |
| 5,433,352 A * | 7/1995 | Ronvig | 222/391 |
| 5,570,821 A * | 11/1996 | DeJonge | 222/391 |
| 6,357,945 B1 * | 3/2002 | Losier et al. | 401/175 |
| 6,599,272 B1 * | 7/2003 | Hjertman et al. | 604/209 |
| 7,011,234 B2 * | 3/2006 | Stradella | 222/129 |
| 7,306,125 B2 * | 12/2007 | Takahashi et al. | 222/391 |
| 2004/0206783 A1 * | 10/2004 | Danne et al. | 222/390 |
| 2007/0131721 A1 * | 6/2007 | Fritschi et al. | 222/391 |
| 2008/0041880 A1 * | 2/2008 | Babineau et al. | 222/146.5 |
| 2008/0114305 A1 * | 5/2008 | Gerondale | 604/207 |
| 2008/0131191 A1 * | 6/2008 | deVirag et al. | 401/171 |
| 2009/0224004 A1 * | 9/2009 | Muller et al. | 222/309 |
| 2009/0234299 A1 * | 9/2009 | Nielsen | 604/228 |
| 2013/0046250 A1 * | 2/2013 | Bode | 604/228 |

* cited by examiner

DRIVE MECHANISM FOR A DRUG DELIVERY DEVICE

CROSS REFERENCE TO RELATED APPLICATIONS

The present application claims priority to European Patent Application No. 10191803.5 filed Nov. 19, 2010, the entire contents of which are incorporated herein by reference.

FIELD OF THE INVENTION

The present invention relates to a drive mechanism for a drug delivery device that allows a user to select single or multiple doses of an injectable medicament and to dispense the set dosage of the medicament as well as to apply said medicament to a patient, preferably by injection. In particular, the present invention relates to such devices, which are handled by the patients themselves.

BACKGROUND

Drug delivery devices allowing for multiple dosing of a required dosage of a liquid medicinal product, such as liquid medicaments, and further providing administration of the liquid to a patient, are as such well-known in the art.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicament to be administered is provided in a cartridge that has a moveable piston or bung mechanically interacting with a piston rod of a drive mechanism of the drug delivery device. By applying thrust to the piston in distal direction, a certain amount of the medicinal fluid is expelled from the cartridge.

With many drug delivery devices of pen-injector type, a user has to depress a dose button, typically located at a proximal end section of the pen housing, in an axial distal direction. In practical use, the dose button is typically to be depressed by a user's thumb while the residual fingers of the same hand grip the housing of the drug delivery device. Furthermore, where an injection force is exclusively to be derived from a user-applied driving force, the handling of a proximal dose button can become problematic, in particular for users suffering side effects or being otherwise handicapped to press the dose button, e.g. by way of a thumb.

OBJECTS OF THE INVENTION

It is therefore an object of the present invention, to provide a drug mechanism for a drug delivery device, wherein a dose button can be depressed also by other fingers than a thumb. It is a further aim to improve the general handling of a drug delivery device, which should be intuitive in understanding. Additionally, the drive mechanism should be robust and reliable in construction as well as cost efficient in production.

SUMMARY

The drive mechanism according to the present invention is designed for a drug delivery device and in particular for a pen-type injector. The drive mechanism comprises a housing or housing component of the drug delivery device which is of substantially cylindrical geometry and which has a long axis extending in an axial direction. The drive mechanism further has an at least axially displaceable piston rod adapted to become operably engaged with a piston of a cartridge containing the medicament. The cartridge, typically designed as a carpule or vial comprises an inner volume being at least partially filled with the medicament to be dispensed.

In proximal direction, hence facing towards the piston rod, the inner volume of said cartridge, is confined and sealed by the piston being moveably disposed in the cartridge. By operably engaging piston rod and piston of the cartridge, the latter can be axially and distally displaced for expelling a pre-defined amount of the liquid medicament, typically from a distal end section of the cartridge, which is further adapted to be coupled with a piercing element like a hypodermic needle assembly for administering the dose of the medicament by way of injection.

The drive mechanism of the drug delivery device further comprises at least one actuation means being radially displaceable with respect to the housing and/or with respect to the piston rod. Radial displacement of the actuation means can be attained by applying a radially inwardly directed depressing force to the actuation means. The actuation means is in turn adapted to transfer a respective driving force to the piston rod.

Moreover, the drive mechanism comprises a coupling means operably engaged with the actuation means and being operably engaged with the piston rod. By way of the coupling means, an externally applied radially inwardly directed depressing force acting on the at least one actuation means can be transferred into a distally directed axial displacement of the piston rod. Hence, the at least one coupling means serves as a transmission for transferring a radially inwardly directed and externally driven displacement of the actuation means into an axial displacement of the piston rod.

By providing at least one actuation means being radially displaceable with respect to the housing, the user may even make use of an arbitrary finger of his hand for applying a required depressing force on the actuation means. This way, the drug delivery device and its drive mechanism can also be operated by a user having otherwise problems with exerting an axially and distally directed depressing force on a proximally located dose button. Also, by way of the radially displaceable actuation means, the axial position of the actuation can be almost arbitrarily chosen, which provides an increased degree of design freedom.

In a preferred embodiment, the coupling means comprises a drive member being threadedly engaged with the piston rod or being threadedly engaged with a drive sleeve. Here, the drive member may comprise a gear meshing or being engaged with the at least one actuation means. Preferably, the actuation means comprises a toothed or geared section, which in response of a radially inwardly directed depression of the actuation means becomes radially displaced with respect to the drive member, thereby inducing a rotational movement on the drive member.

In a further preferred embodiment, the at least one actuation means comprises a toothed section engaged with an outer gearing of the drive member, the drive sleeve or of the piston rod.

The drive member may be integrally formed with the drive sleeve. Also, drive sleeve and piston rod may be designed as separate mutually engaged parts or may be integrally formed and may therefore comprise a single, shaft-like rod axially guided in the housing, e.g. by way of a spindle nut threadedly or otherwise positively engaged with a corresponding outer thread of the piston rod.

In another preferred aspect, the drive sleeve and/or the drive member is axially fixed and rotatably mounted in the housing. This way, a substantially translational, radially inwardly directed driving force applied to the actuation means is preferably transferred into a pure rotational motion of the drive sleeve and/or the drive member.

In still another aspect, the drive sleeve is threadedly engaged with the piston rod, which is at least axially displaceable with respect to the housing. Depending on its contour, preferably corresponding with a respective guiding member of the housing, it is even conceivable, that the piston rod is rotatably fixed with respect to the housing and/or that the piston rod is both, rotatably and axially displaceable with respect to the housing. By having a threaded engagement of drive sleeve and piston rod, a required transmission of a rotational movement can still be provided. Depending on the type of gearing implemented here, the speed of rotation of the drive sleeve and that of the piston rod may vary accordingly.

In another preferred aspect, the actuation means and the drive sleeve, and/or the drive member, are unidirectionally coupled with respect to each other in such a way, that only a radially inwardly directed displacement of the actuation means has a rotational effect on the drive sleeve or its drive member, respectively. Preferably, unidirectional coupling of actuation means and drive sleeve or drive member provides a kind of a ratchet mechanism, wherein in another preferred embodiment, a displacement of the actuation means from an inner end position to an outer activated position is substantially effectless on the drive member and the drive sleeve.

For instance, a toothed section of the actuation means comprises a saw-toothed profile exclusively adapted to induce a rotational motion to a drive member in response to a radially inwardly directed displacement.

In another preferred aspect, the at least one actuation means is spring biased radially outwardly. Hence, a transfer and radial displacement of a dose button as actuation means from an inner end position to an outer actuation configuration is supported by the effect of a spring or a comparable mechanical force storing assembly.

This way, the actuation means, e.g. a respective dose button autonomously transfers into an active position when released, e.g. by way of an activation means, such as an activation button.

According to another preferred embodiment, the actuation means comprises two substantially diametrically opposed dose buttons protruding from a lateral side wall section of the housing in an activation position or position of use. Having two oppositely arranged dose buttons, a depressing force can be rather easily applied thereto, e.g. by applying oppositely directed pressure to the two buttons, which is comparable to a gripping motion, wherein for instance one button is depressed by an index or middle finger whereas the other button is depressed by a thumb or ball of the thumb. This way, an ergonomic and variable handling of a respective drug delivery device can be provided. Moreover, in this configuration the mutually opposed and externally applied depressing forces can equally serve to set the drive member in rotational movement.

In another embodiment, it is further of advantage, when the dose buttons comprise a radially inwardly facing toothed protrusion meshing with respective geared sections of the drive member. Hence, the dose button as seen in a lateral plane perpendicular to the elongation of the piston rod may comprise an L-like shape, wherein radially directed and toothed protrusions are threadedly engaged and mesh with opposite side sections of the drive member, whereas the dose button itself extends in the lateral plane in radial outward direction.

In still another aspect, the at least one actuation means is locked in position in a radial inward end position by means of at least one interlock member. Typically, at the end of a dose dispensing procedure, the actuation means, hence the dose button, reaches a radially inwardly located end section, in which, e.g. by way of a latching or interlock element, the dose button is secured and kept in said end position, in which a dispensing of a dose of the medicament is substantially impeded and thus not possible.

Preferably by way of an activation means, said latch or interlock can be released and the dose button may autonomously displaced in the radially outwardly located activated position, e.g. under the effect of the spring element.

According to a further embodiment, the interlock member comprises a radially outwardly protruding flap or tongue being flexibly deformable in axial direction. Preferably, said flap or tongue is adapted to radially but against an inward facing side wall section of the housing when the dose button reaches its end position. By this radial abutment, the dose button can be retained in its radially inwardly located end position.

If the protruding tongue is disposed on a proximal end face of the dose button, in a further preferred embodiment, an activation means will be axially displaceably mounted at a proximal end section of the housing relative to the housing for axially depressing the free end of the tongue into a release configuration, in which radial abutment of the tongue with respect to the housing is abrogated. Furthermore and as a consequence, the dose button may autonomously displace in its radial outward activated position.

In an alternative embodiment, wherein the radially outwardly protruding tongue is disposed on a distal end face of the actuation means, i.e. of the dose button, the activation means is arranged distal to the actuation means and is further adapted to be displaced in proximal direction for depressing the tongue's or flap's free end in a respective release configuration.

Apart from the described interlock mechanism it is also conceivable to make use of other positive- and/or frictionally engaged interlock and latching mechanisms.

Moreover and in another independent aspect, the invention also relates to a drug delivery device for dispensing a dose of a medicament, wherein the device comprises a drive mechanism as described above and further has at least a cartridge comprising a moveable piston to be engaged with a piston rod of the drive mechanism. Here, the piston is sealing an inner volume of the cartridge being at least partially filled with the medicament.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE FIGURES

Without limitation, the present invention will be explained in greater detail below in connection with preferred embodiments and with reference to the drawings in which.

DETAILED DESCRIPTION

Figure 1:
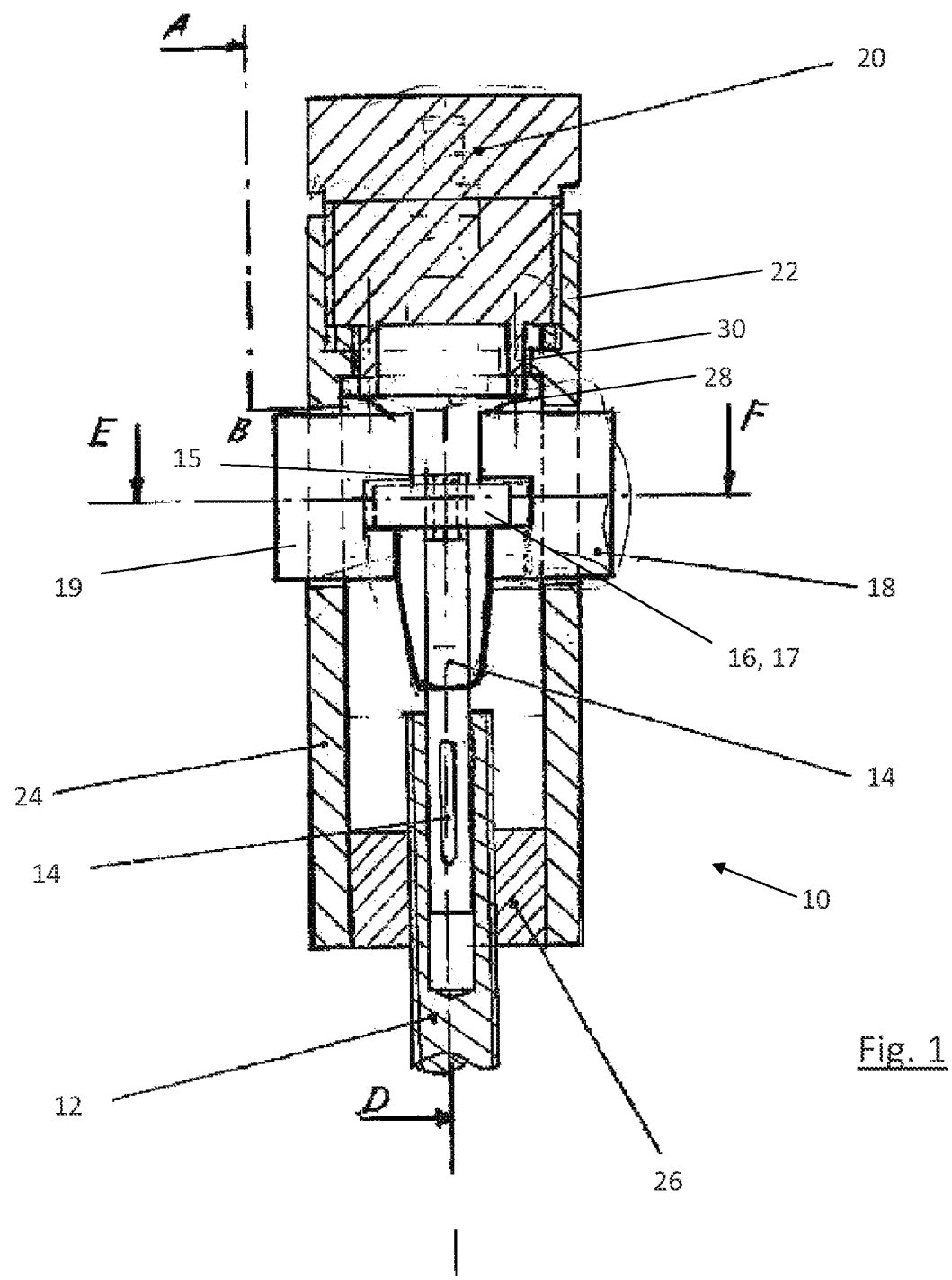
FIG. 1 schematically illustrates the drive mechanism according to the present invention in a longitudinal cross section.

As illustrated in FIGS. 1 to 4, the illustrated drive mechanism 10 is adapted to be used and implemented with a drug delivery device, in particular with a pen-type injector. The illustrated drive mechanism 10 comprises a housing 22, 24, in which by way of a nut 26, a piston rod 12 is axially guided. The piston rod 12 is in turn adapted to become engaged with a piston of a medicament-filled cartridge, which is not explicitly illustrated here. As illustrated, the housing comprises a distal housing section 24 and a proximal housing section 22, which may be separately or integrally formed.

The piston rod 12 is typically threadedly engaged with the nut 26 but may also be rotatably locked to the nut 26, e.g. when the piston rod 12 comprises an axial groove or protrusion corresponding with a respective radially directed protrusion or groove of the nut 26. Therefore, mutual engagement of nut 26 and piston rod 12 may support or inhibit rotational movement of the piston rod 12 relative to the housing in the course of an axial displacement.

Figure 2:
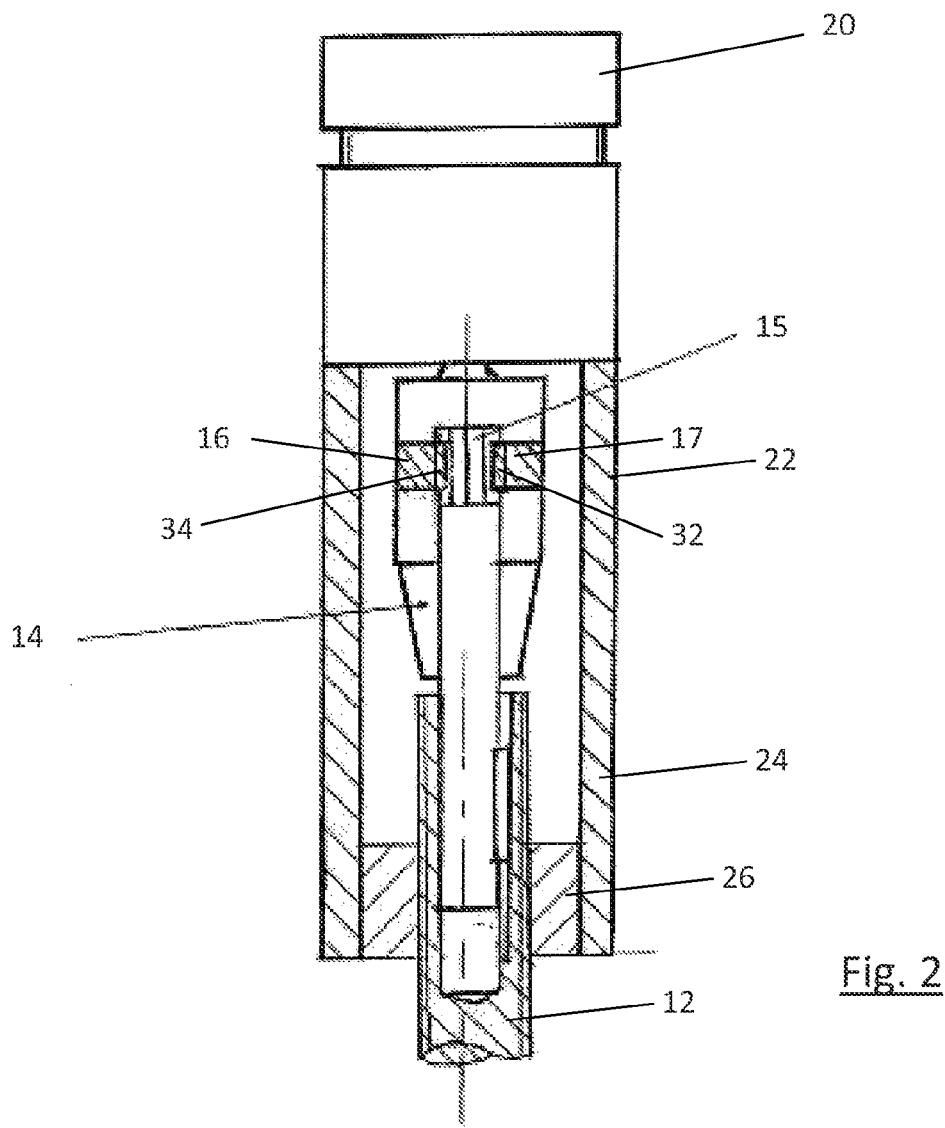
FIG. 2 is illustrative of the drive mechanism according to FIG. 1 along a cross section A-D as indicated in FIG. 1.
Figure 3:
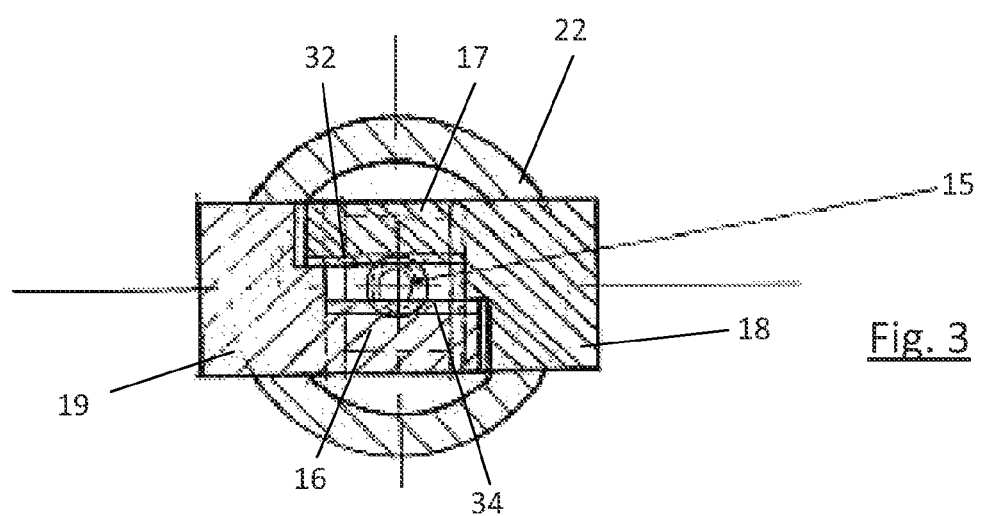
FIG. 3 shows a cross section along E-F as depicted in FIG. 1.

As further illustrated, the piston rod 12 is threadedly engaged with a drive sleeve 14, which, at its proximal end, facing upward in FIGS. 2 and 3, is connected or integrally formed with a drive member 15. The drive member 15, typically designed as a gear with a circumferential toothing meshes with respective geared or toothed sections 32, 34 of lateral protrusions 16, 17 of the two dose buttons 18, 19 as illustrated in FIGS. 1 and 3.

Here, the laterally extending and rather rectangularly shaped protrusions 16, 17 comprise a toothed side surface 32, 34 facing towards and meshing with opposite side sections of the drive member 15. The mechanical coupling of the lateral protrusions 16, 17 with the drive member 15 and/or a mechanical connection between drive member 15 and drive shaft or drive sleeve 14 is unidirectional. Hence, when the protrusions 16, 17 and their respective dose buttons 19, 18 are displaced radially outwardly into an activation position or position of use, the position and orientation of the drive sleeve 14 remains substantially unaffected.

However, in the opposite direction, when an externally applied actuation force depresses the two dose buttons 18, 19 radially inwardly, the threaded or geared engagement of the protruding portions 16, 17, the drive member 15 and/or its associated drive sleeve 14 is active in order to transfer the radially inwardly directed displacement of the dose button 18, 19 into a respective rotation of the drive sleeve 14. By way of a respective threaded engagement of drive sleeve 14 and piston rod 12, the piston rod 12 becomes respectively displaced in distal direction for the purpose of dispensing a predefined dose of the medicament.

In FIG. 2, said lateral protrusions 16, 17 are illustrated in longitudinal cross section rotated by 90° compared to the illustration according to FIG. 1. As shown here, the lateral protrusions 16, 17 and respective dose buttons 18, 19 mesh with the drive member 15 by way of radially inwardly facing toothed sections 32, 34.

Further, with reference to FIGS. 1 and 3, the purely radially displaceable dose buttons 18, 19 protrude from a lateral circumference of the housing 22, 24, wherein an upper housing section 22 is further adapted to receive an activation button 20. Depressing said activation button 20 against the action of a flexibly deformable latching member 28 releases the dose buttons 18, 19, which become thus enabled to be displaced to a radial outward position of use, which is not explicitly illustrated in the Figures.

Figure 4:
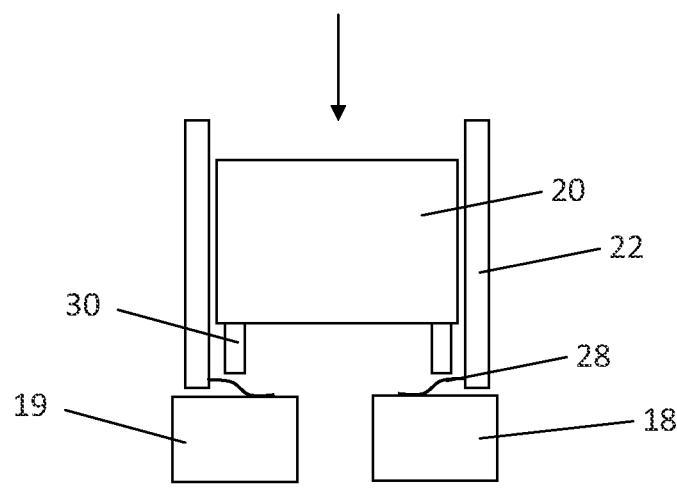
FIG. 4 illustrates an enlarged cross section of a latching mechanism.

As further illustrated in the enlarged view according to FIG. 4, the latching means 28 comprises at least a radially and proximally protruding tongue 28 elastically deformable in axial direction. In its interlock configuration as shown in FIG. 4, the tongue 28 with its free and radially outwardly protruding end section buts against an inward facing side wall section of the housing section 22. As soon as the activation button 20 is depressed by an external force as illustrated by the arrow in FIG. 4, the radially and proximally protruding free end of said tongue or flap 28 becomes elastically deformed in distal direction. This way said radial abutment can be abrogated and the dose buttons 18, 19 may autonomously displace into an outer position of use, e.g. under the effect of a not explicitly illustrated spring element, whereby the free end of the tongue 28 enters the axial slit between housing 22 and dose button 18, 19.

The invention claimed is:

1. A drive mechanism of a drug delivery device for dispensing of a dose of a medicament, comprising:
   a housing of substantially cylindrical geometry having a long axis extending in an axial direction, the housing having a distal portion and a proximal portion,
   a nut axially and rotationally fixed to an inner surface of the distal portion of the housing;
   an at least axially displaceable piston rod adapted to become operably engaged with a piston of a cartridge containing the medicament for displacing the piston in a distal direction, where the piston rod and the nut are configured such that the piston rod moves axially in the distal direction relative to the nut during dose delivery, two diametrically opposed dose buttons protruding from a lateral side wall of the housing at a location defining a transition between the distal and proximal housing portions when the buttons are in an activation position, where at least one dose button is radially displaceable with respect to the housing by an externally applied depressing force for transferring a respective driving force to the piston rod, an activation button is located at a proximal end of the proximal housing portion and is axially displaceable relative to both the housing and the two dose buttons, where the activation button is configured to cause the two dose buttons to move radially from an end position to the activation position when the activation button is moved distally, and a coupling located adjacent the nut operably engaged with the dose buttons and with the piston rod, where the coupling is configured to transfer the radially inwardly directed displacement of the at least one dose button into a distally directed axial displacement of the piston rod, characterized in that the coupling comprises a drive member threadedly engaged with the piston rod or with a drive sleeve.

2. The drive mechanism according to claim 1, wherein the at least one dose button comprises a toothed section engaged with an outer gearing of the drive member or of the piston rod.

3. The drive mechanism according to claim 1, wherein the drive sleeve and/or drive member is axially fixed and rotatably mounted in the housing.

4. The drive mechanism according to claim 1, wherein the drive sleeve is threadedly engaged with the piston rod being rotatably fixed and axially displaceable with respect to the nut.

5. The drive mechanism according to claim 1, wherein the dose buttons and the drive sleeve are unidirectionally coupled with respect to each other in such a way that only a radially inwardly directed displacement of the at least one of the dose buttons has a rotational effect on the drive sleeve.

6. The drive mechanism according to claim 1, wherein the at least one dose button is spring biased radially outwardly.

7. The drive mechanism according to claim 1, wherein the dose buttons comprise a radially inwardly facing, toothed protrusion meshing with diametrically opposite geared sections of the drive member.

8. The drive mechanism according to claim 1, wherein the at least one dose button is locked in position in a radial inward end position by means of at least one interlock member.

9. The drive mechanism according to claim 8, wherein the interlock member comprises a radially outwardly protruding tongue flexibly deformable in axial direction and being adapted to but against an inward facing side wall section of the housing in radial direction when the dose button is in its end position.

10. The drive mechanism according to claim 9, wherein an activation button is axially displaceably mounted in the proximal section of the housing for axially depressing the free end of the tongue into a release configuration.

11. A drug delivery device for dispensing a dose of a medicament comprising:

a drive mechanism according to claim 1, and a cartridge comprising a movable piston to be engaged with a piston rod of the drive mechanism, the piston sealing an inner volume of the cartridge being at least partially filled with the medicament.

* * * * *